United States Patent [19]

Shields

[11] Patent Number: 4,932,946

[45] Date of Patent: Jun. 12, 1990

[54] HUB-MOUNTED, SLIT-ELASTIC NEEDLE GUARD

[76] Inventor: Jack W. Shields, 1950 Las Tunas Rd., Santa Barbara, Calif. 93103

[21] Appl. No.: 266,134

[22] Filed: Jul. 29, 1988

[51] Int. Cl.$^5$ ............................................. A61M 5/32
[52] U.S. Cl. ..................................... 604/198; 604/263
[58] Field of Search ................ 604/163, 197, 198, 263

[56] References Cited

U.S. PATENT DOCUMENTS

| | | | |
|---|---|---|---|
| 3,658,061 | 4/1972 | Hall | 604/263 |
| 4,643,722 | 2/1987 | Smith, Jr. | 604/263 |
| 4,747,836 | 5/1988 | Luther | 604/263 |

FOREIGN PATENT DOCUMENTS 0002 6/1987 Sweden .
0001 10/1986 United Kingdom .

OTHER PUBLICATIONS

Morbidity and Mortality Weekly Report, Jun. 24, 1988, vol. 37, No. 24, Publ. by the Massachusetts Medical Society, pp. 377–388.

Primary Examiner—Stephen C. Pellegrino
Attorney, Agent, or Firm—Michael G. Petit

[57] ABSTRACT

Intravenous needle sheaths are described which can be used safely for exposing the recapping the sharp tips. The sheaths comprise partially slit concentric or eccentric elastic tubes with special markings, the proximal ends of which are anchored permanently to the hubs of various kinds of needles, and the distal ends of which guide the tips safely through combinations of rigid and elastic parts in all positions of needle exposure, use and resheathing.

15 Claims, 3 Drawing Sheets

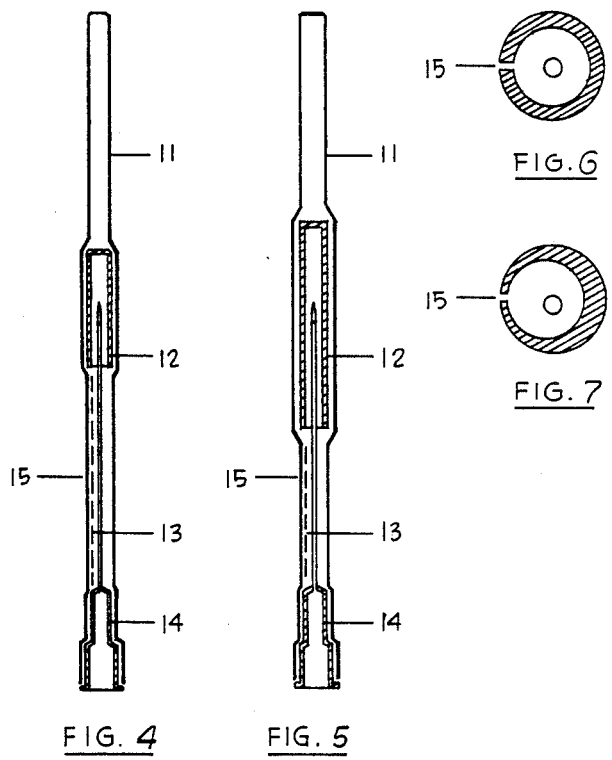

HUB-MOUNTED, SLIT-ELASTIC NEEDLE GUARD

BACKGROUND OF THE INVENTION

1. Field of the Invention.

The invention relates to permanently attached needle guards or sheaths.

2. Description of the Prior Art.

contaminated blood from infected persons is a common source of HIV and HBV virus infecitions in health care workers. (See Morbidity and Morality Weekly Report, Jun, 24, 1988, Vol. 37 No. 24, pp. 377-388). Infection control must focus on needle safety, the appropriate use of gloves and immunizations whenever available. Although aseptic procedures and gloves protect such workers, these cannot uniformly prevent needle-stick injuries with contaminated blood.

Needles and needle/syringe combinations are now almost routinely sheathed in tapered or non-tapered, closed or open end, rigid plastic sheaths which are discarded after the needle is exposed. After use, no attempt is made to resheath the needle because too many needle-stick injuries result. Instead, the needles, butterfly assemblies, infusion sets, syringe/needle combinations or double-ended needles from vacutainer systems are disposed as soon as possible into rigid safety containers which may, or may not, be readily available.

The accordion needle sheath developed by Peters in Great Britain and described in International Patent Application Number: PCT/GB86/00194 filed 8 Apr., 1986, has not achieved popular use, apparently for three reasons:

(a) it is relatively expensive to manufacture, owing to the complexity and possible slippage of parts;

(b) the elastic components of the system theoretically work against resheathing the needle; and (c) the user muse use his fingers perilously close to the tip of the needle to sheath or resheath.

A slit, but rigid and hinged plastic sheath developed in Sweden (Sweden Application Number 8505880-8 filed Dec. 12, 1985) has not achieved popular use, apparently for two reasons:

(a) proximal attachment of the slit sheath would require too many modifications of standard needle hubs, thus precluding manufacture in quantity for all kinds of needles or needle/syringe assemblies.

(b) when unhinged, the sheath might be awkward to use especially with butterfly and vacutainer systems.

The instant invention combines the elasticity of the durable elastomeric tubing now available with the slit by means of which one can expose or resheath the needle, to form a permanently tethered needle sheath which is an inexpensive, adjunct to needle safety wherever rigid steel needles are employed to withdraw blood or give injections, especially into veins.

This invention relates to permanently tethered needle sheaths made of elastic and rigid materials through which slits are made to expose and safely resheath hollow needles used for drawing blood or administering intravenous medications. One object of this invention is to provide a needle guard which will minimize the risk of "needle-stick" injuries to medical personnel and other persons after blood specimens or tissue fluids potentially containing infections agents, especially AIDS and serum hepatitis viruses, have been withdrawn from individuals requiring tests or treatment. A further object of this invention is to provide a useful, safer needle sheathing system which can be produced at minimal cost to the manufacturer, as well as the user.

SUMMARY OF THE INVENTION

Needle sheaths are described which can be safely used to expose and resheath hollow intravenous needles. The sheaths comprise partially slit elastic tubes, the proximal ends of which are anchored permanently to the needle hubs, while the distal ends contain rigid plastic sleeves to safely house the sharp tips when the needles are not in use. Beyond the rigid sleeves, which may be capped or uncapped, the elastic tubing extends beyond the tip of the needle to allow easy and safe manipulation of the assembly during needle exposure, use for injections or drawing blood and immediate resheathing of the needle.

An outstanding safety feature is that there is substantially no lag time after the user withdraws the needle from the vein of a subject until the needle is capped. As soon as he/she lets go of the tip of the elastic tube, the tube immediately and automatically recoils back into place for resheathment of the entire needle. Gentle traction at the distal end of the assembly rehouses the needle tip within its rigid puncture-proof housing. Subsequently, the needle, tubing, syringe or double-tipped vacutainer needle can be transported to the nearest safe container with minimal chance of straight on or tangential needle-stick injury to the user or anyone located nearby.

BRIEF DESCRIPTION OF DRAWINGS

FIG. 4: A magnified cutaway view of the positioning of the rigid plastic cap or sheath housed within the elastic tubing relative to the slit, the rigid portion and the needle tip.

FIG. 5: An alternative version wherein the rigid inner sheath is not capped, but extended beyond the potential projection of needle if the assembly is collapsed toward the needle hub.

FIG. 6: A cross section through a concentric elastomeric tube at the level of the slit of a first preferred embodiment.

FIG. 7: A cross section through an eccentric elastomeric tube at the level of the slit in a second preferred embodiment.

DESCRIPTION OF THE PREFERRED EMBODIMENT

A. First Preferred Embodiment

Figures 1, 2, 3:
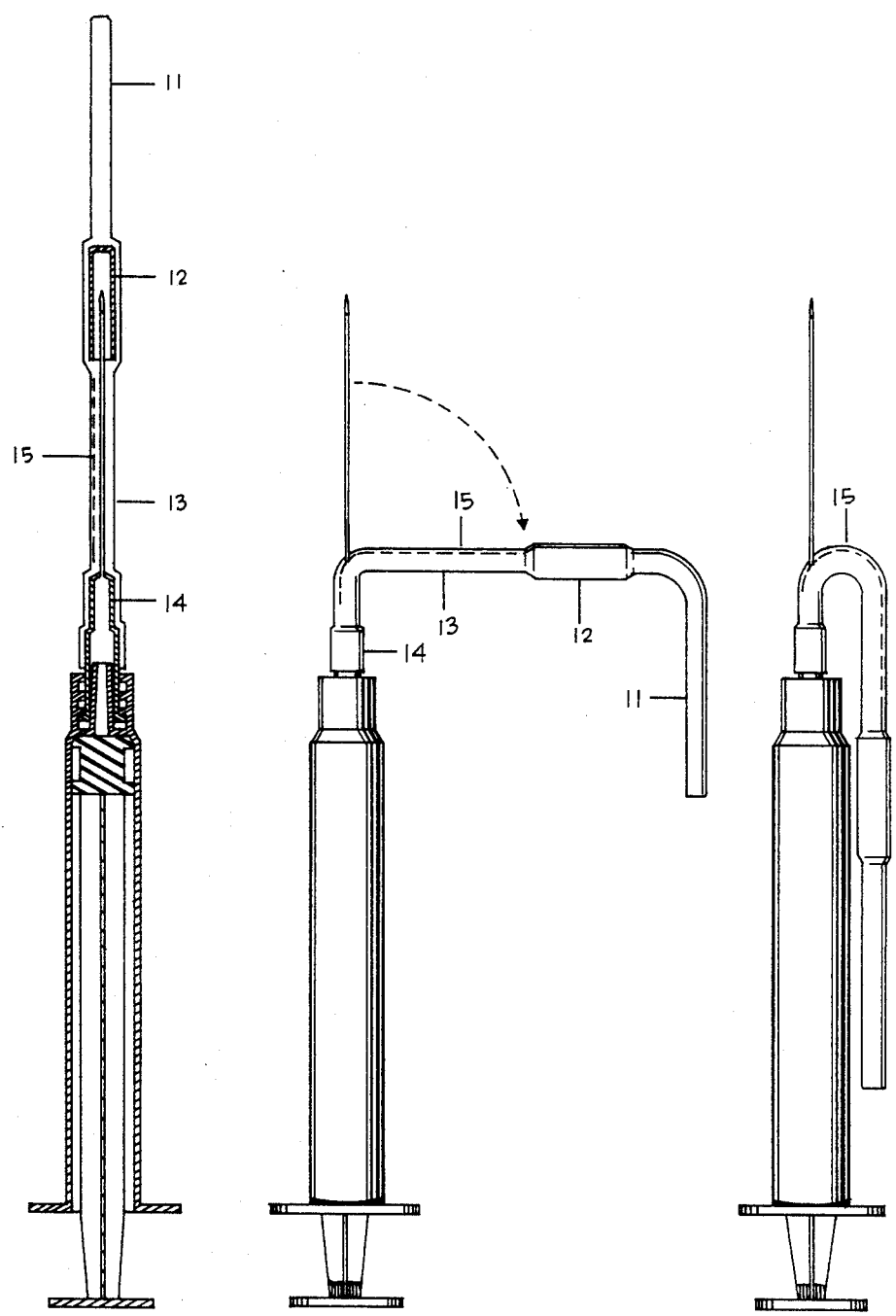
FIG. 1: A cutaway schematic view of the intravenous needle sheath of the present invention protecting a standard needle (left) or butterfly needle (right).
FIG. 2: A schematic representation of the sheath of FIG. 1 opening to expose the needle tip.
FIG. 3: A schematic view of the needle sheath of FIG. 1 with the sheath folded back to expose the entire needle. During needle insertion into a vein, the tip of the sheath is grasped between the closed wings of butterfly needles, or alongside the barrels of syringes and vacutainer systems, as depicted below.
Figure 8:
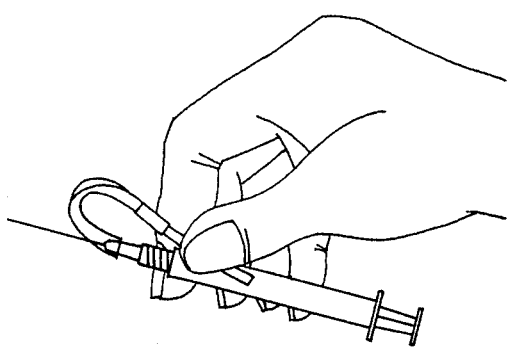
FIGS. 8 (a,b,c): Action drawing showing the first preferred embodiment being used to expose a needle prior to use.
Figure 8:
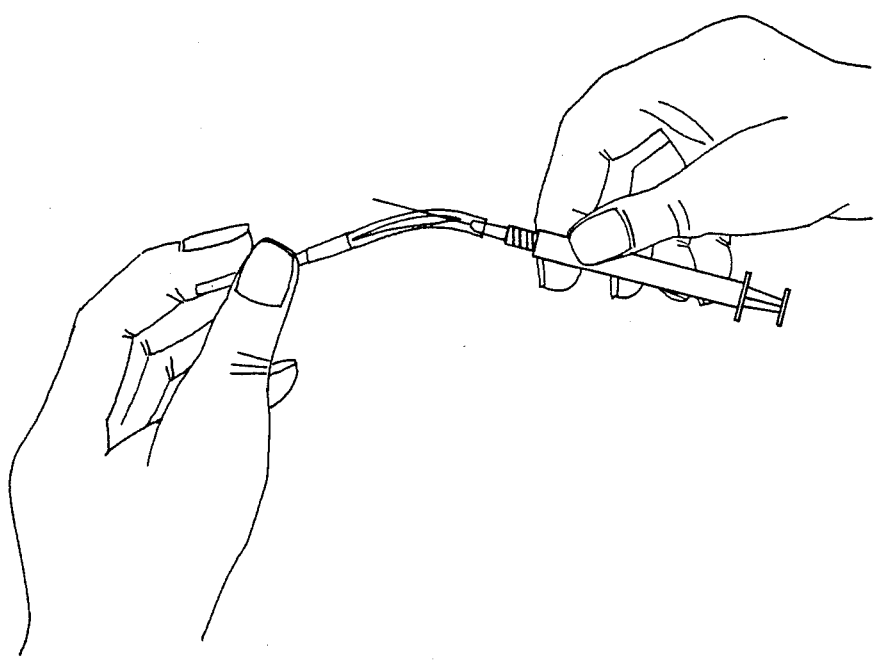
Figure 8:
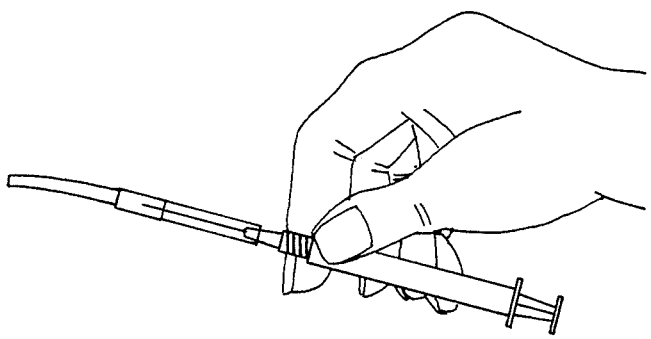

The hypodermic needle sheath comprising the first preferred embodiment of the present invention can best be understood by looking first at FIG. 1. The sheath comprises a single section of elastomer tubing having a proximal end (13) permanently effixed to a needle hub (14) and a distal end (11). Interposed within the lumen of the tubing is a protective cap (12) positioned to cover the tip of the needle when the sheath is closed (FIG. 4). A slit (15) in the proximal segment of the sheath tubing (13) permits the sheath to be removed from the needle by (a) applying gently tension on the distal end of the sheath and (b) bending the sheath so that the needle emerges through the slit (15) as shown schematically in FIG. 2 and FIG. 3. The needle tip may be recapped by reversing the procedure. Due to the elasticity of the proximal end of the sheath (13) when the distal end is released as a prelude to sheathing the needle, the sheath will assume as position substantially parrallel to the needle. Gentle tension on the distal end (11) permits the needle to be guided through the slit (15) into the interior lumen of the sheath. Relaxing the tension on the distal end completes the resheathing by seating the needle tip safely within the interior of the protective cap (12). The above sequence of motions required for exposing a needle is shown in FIG. 8. Resheathing the needle is accomplished by reversing the steps.

B. Second Preferred Embodiment

A second preferred embodiment is similar to the first except that the protective cap (12) is open on both ends (FIG. 5). Since the proximal end of the sheath (12) is not compressible, a needle sheath with this protective cap is resistant to straight-on needle pricks and immune to tangential needle pricks.

C. Other Perferred Embodiments

During needle use, the normal position for the sheath is bent back away from the needle and secured in position by restraining means. When the needle is withdrawn from a patient and is desirably resheathed, the restraint securing the sheath in the bent-back position is removed and the sheath snaps back against the needle thus providing a degree of immediate protection against accidental needle pricks. It is desirable that the elasticity of the proximal end of the needle protective cap be sufficient to hold the sheath snugly snugly against the needle. The elasticity of the sheath in either of the first two embodiments may be improved still further by differentially reinforcing the wall on the proximal end of the sheath (13) on the side opposite the slit as shown in FIG. 7. FIG. 6 shows the proximal end of the sheath tubing wherein a concentric wall surrounds the needle (19) whereas the tubing of FIG. (7) presents an eccentric wall about the needle.

The foregoing embodiments are provided to instruct in the use of the invention. The scope of the invention is not limited to the particular embodiment described above.

What I claim is:

1. A needle sheath for preventing accidental needle sticks comprising: (a) an elastomer tube containing a lumen of sufficient size to house a needle within said lumen, one end of said tube being concentrically affixed to the hub of said needle; and (b) a hollow substantially cylindrical protective cap containing an interior chamber, said protective cap being permanently disposed within said lumen of said tube such that the sharp tip of said needle is within in interior chamber of said protective cap when said needle is sheathed thereby protecting the needle user from end-on accidental needle sticks; and (c) a slit in the wall of said tube, the direction of said slit being parallel to said lumen and extending substantially from said protective cap to said needle hub to permit passage of said needle through the wall of said tube when said tube is extended.

2. The sheath of claim 1 wherein said protective cap is made of a material resistant to puncture by a hypodermic needle.

3. The sheath of claim 2 wherein said elastomeric tube is silicone.

4. The sheath of claim 2 wherein said elastomeric tube is latex.

5. The sheath of claim 2 wherein said elastomeric tube is polyethylene.

6. The sheath of claim 2 wherein the length of said slit is 50-95% of the length of said needle.

7. The sheath of claim 2 further comprising an optically visible slit-delineating marker on the wall of said tube contiguous with said slit.

8. A needle sheath comprising (a) a substantially cylindrical protective cap to protect a user from accidental end-on needle stick injury, said cap containing an open end and a closed end, the open end of said cap being permanently affixed to a length of elastomeric tubing, said tubing having a longitudinal slit wall extending substantially parrallel to the long axis of said tubing, said slit providing means to permit exposure of a hypodermic needle contained within the lumen of said tubing; and (b) a tab providing means for grasping said sheath affixed to the closed end of said protective cap.

9. The sheath of claim 8 in which said elastomeric tubing is silicone.

10. The sheath of claim 8 in which said elastomer tubing is polyethylene.

11. The sheath of claim 8 in which said elastomer tubing is latex.

12. The sheath of claim 8 wherein the length of said slit is 50-95% of the length of the needle.

13. The sheath of claim 8 wherein said tub is an extension of said elastomeric tubing, said extension being of sufficient length to protrude 1-3 inches beyond the closed end of said protective cap.

14. the sheath of claim 8 further comprising an optically visible slit-delineating stripe on the wall of said elastomer tubing parallel to and contiguous with said slit.

15. A permanently anchored tubular elastic needle sheath for minimizing the chances of needle-stick injury, comprising:
  (a) a hollow elastic tube having a proximal end firmly attachable to the hub assembly surrounding a needle used for drawing blood or giving an injection;
  (b) a longitudinal slit in the wall of said tube, said slit being in a direction parallel with the long axis of said tube, said slit providing an opening through which the needle is exposed when the elastic tube is stretched and swung away;
  (c) a distal end significantly longer than the needle, providing means for manually grasping the needle sheath to unsheath and resheath the needle by gentle manual traction in vectors closely aligned. with the long axis of the needle.

* * * * *